(12) United States Patent
Robinson et al.

(10) Patent No.: US 10,092,688 B2
(45) Date of Patent: Oct. 9, 2018

(54) MEDICAMENT KIT AND METHOD OF USE

(76) Inventors: Laura Jean Robinson, Minneapolis, MN (US); Ida Schneck, Minneapolis, MN (US)

(\*) Notice: Subject to any disclaimer, the term of this patent is extended or adjusted under 35 U.S.C. 154(b) by 593 days.

(21) Appl. No.: 13/467,570

(22) Filed: May 9, 2012

(65) Prior Publication Data
US 2012/0289931 A1 Nov. 15, 2012

Related U.S. Application Data

(60) Provisional application No. 61/485,983, filed on May 13, 2011.

(51) Int. Cl.
*A61M 31/00* (2006.01)
*A61M 5/00* (2006.01)
*A61M 5/24* (2006.01)

(52) U.S. Cl.
CPC ............ *A61M 5/002* (2013.01); *A61M 5/003* (2013.01); *A61M 5/2448* (2013.01); *A61M 2205/18* (2013.01); *A61M 2205/58* (2013.01)

(58) Field of Classification Search
CPC ............ A61M 2205/583; A61M 5/002; A61M 5/003; A61M 5/2448; A61M 2005/2451; A61M 2205/58; A61M 2205/581; A61M 2205/183; A61M 2205/582; A61M 5/285; A61M 5/19; A61M 5/02; A61M 2205/18; A61M 2205/55; A24F 15/12
USPC ... 604/66, 82–90, 504, 890.1, 6.1, 189, 218, 604/503, 506, 508, 191; 206/363–370, 206/571; 361/679; 368/10, 12, 278
See application file for complete search history.

(56) References Cited

U.S. PATENT DOCUMENTS

| 380,673 | A | * | 4/1888 | Barton | ................ A61M 5/2425 604/214 |
| 3,836,717 | A | * | 9/1974 | Gagnon | ................ G10L 19/00 704/265 |
| 4,031,893 | A | | 6/1977 | Kaplan et al. | |
| 4,693,706 | A | | 9/1987 | Ennis, III | |

(Continued)

OTHER PUBLICATIONS

Karmel Allison, Glucagon Kits: GlucaPen Aims to Improve Our Emergency Arsenal, http://asweetlife.org, Aug. 5, 2010.

(Continued)

*Primary Examiner* — Kevin C Sirmons
*Assistant Examiner* — Tiffany Legette-Thompson
(74) *Attorney, Agent, or Firm* — Mitchell Hamline IP Clinic

(57) ABSTRACT

A medicament delivery system and method of use. A medicament delivery system comprising a medicament, a medicament delivery device, an alerting device, operating instructions, and a carrying case. The medicament can be glucagon for use with Type 1 diabetics. A method where a person assisting a patient in medical distress locates the patient's medicament injection pen by using an alerting device that sends a signal to the pen's carrying case, and where a triggered alarm in the case alerts the assisting person of the pen's whereabouts. A method where a person assisting a patient in medical distress provides a medicament to the patient by pushing an actuator on a medicament injection pen until a diaphragm separating two chambers in the pen breaks allowing medicament and diluting solution to mix, and where the assisting person then injects the mixture into a soft tissue of the patient.

20 Claims, 8 Drawing Sheets

(56) References Cited

U.S. PATENT DOCUMENTS

| | | | |
|---|---|---|---|
| 5,080,649 A | 1/1992 | Vetter | |
| 5,139,490 A | 8/1992 | Vetter et al. | |
| 5,320,603 A | 6/1994 | Vetter et al. | |
| 5,727,770 A * | 3/1998 | Dennis | A61B 17/3462 251/149.1 |
| 6,419,656 B1 | 7/2002 | Vetter et al. | |
| 6,443,890 B1 * | 9/2002 | Schulze et al. | 600/300 |
| 6,817,987 B2 | 11/2004 | Vetter et al. | |
| 7,615,234 B2 | 11/2009 | Potter et al. | |
| 2002/0016719 A1 * | 2/2002 | Nemeth | G06Q 50/22 705/2 |
| 2003/0036683 A1 * | 2/2003 | Kehr et al. | 600/300 |
| 2003/0038047 A1 * | 2/2003 | Sleva et al. | 206/370 |
| 2003/0187525 A1 * | 10/2003 | Mann et al. | 700/90 |
| 2004/0093167 A1 * | 5/2004 | Braig | A61B 5/0002 702/23 |
| 2004/0243055 A1 * | 12/2004 | Tan | 604/82 |
| 2005/0182358 A1 * | 8/2005 | Veit et al. | 604/93.01 |
| 2006/0042139 A1 * | 3/2006 | Mendes | 40/633 |
| 2006/0142057 A1 * | 6/2006 | Schuler et al. | 455/556.1 |
| 2008/0033393 A1 * | 2/2008 | Edwards | A61M 5/2033 604/503 |
| 2008/0132852 A1 * | 6/2008 | Kleyhan | A61M 5/31595 604/210 |
| 2008/0139910 A1 * | 6/2008 | Mastrototaro et al. | 600/365 |
| 2008/0146998 A1 * | 6/2008 | Bertron et al. | 604/89 |
| 2008/0198012 A1 * | 8/2008 | Kamen | 340/572.1 |
| 2009/0062740 A1 * | 3/2009 | Thorne, Jr. | 604/191 |
| 2009/0099505 A1 * | 4/2009 | Hendrixson | A61M 5/14244 604/48 |
| 2009/0299328 A1 * | 12/2009 | Mudd et al. | 604/506 |
| 2011/0034791 A1 * | 2/2011 | Moerman | A61B 5/0022 600/347 |
| 2011/0060274 A1 | 3/2011 | Kuhn | |

OTHER PUBLICATIONS

Amy Tenderich, Enject's GlucaPen: Diabetes' Answer to the EpiPen, http://www.diabetesmine.com, Jul. 9, 2010.

Michael Flanagan, To the rescue, http://www.enject.com/uploads/Enject_article_BioCentury.pdf; www.biocentury.com, May 4, 2009.

Tim Welch, New Technology for Administering Glucagon Could Assuage Schools' Fears, Save Children's Lives, http://blogs.kentlaw.edu, Mar. 20, 2009.

Bernard Farrell, The GlucaPen, a big improvement on Glucagon shots, http://www.bernardfarrell.com, Mar. 17, 2009.

Enjectinc, GlucaPen Diabetesmine Entry, http://www.youtube.com/user/enjectinc, Apr. 17, 2009.

Dey Pharma, L.P., How to Use EpiPen, http://www.epipen.com/how-to-use-epipen, 2010.

Ikeyless, LLC, iKeyless Key Finder, https://www.ikeyless.com/store/product/view/?id=1001552, 2011.

* cited by examiner

200

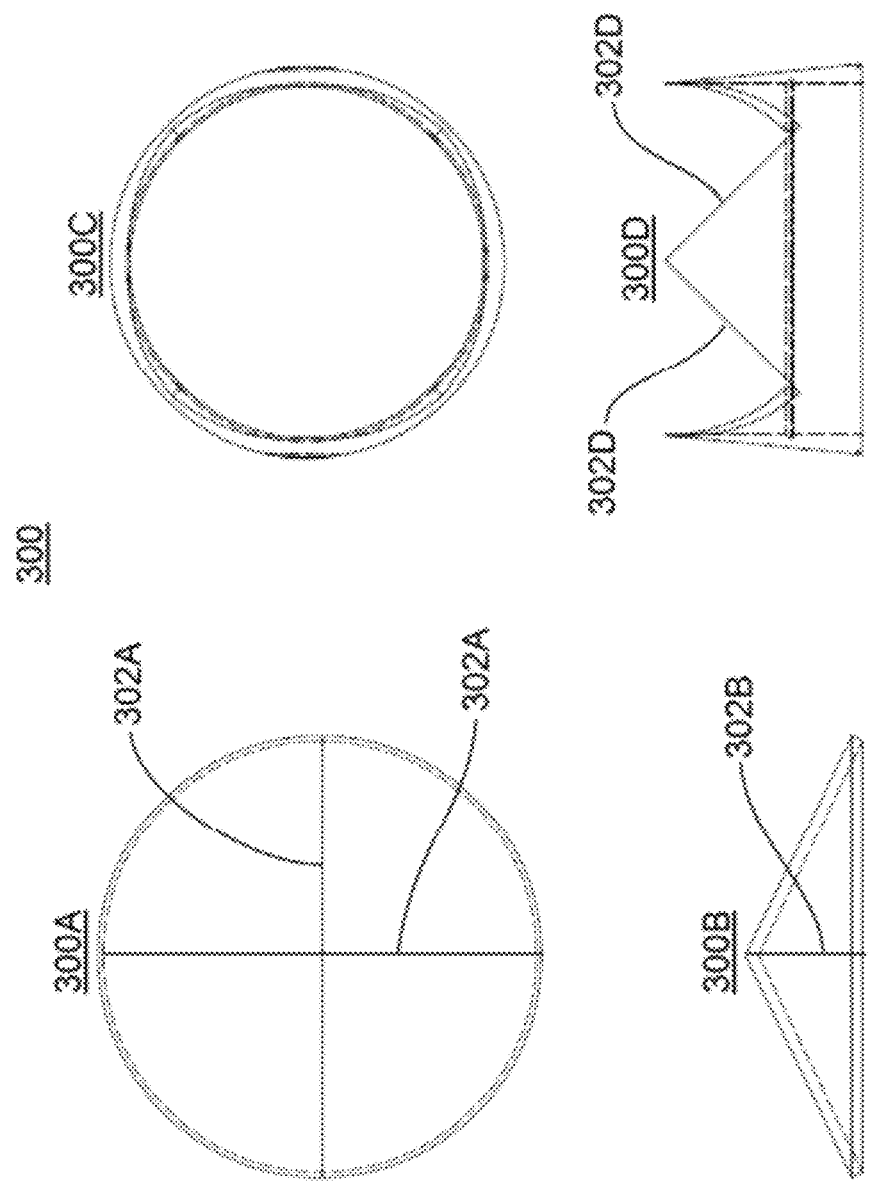

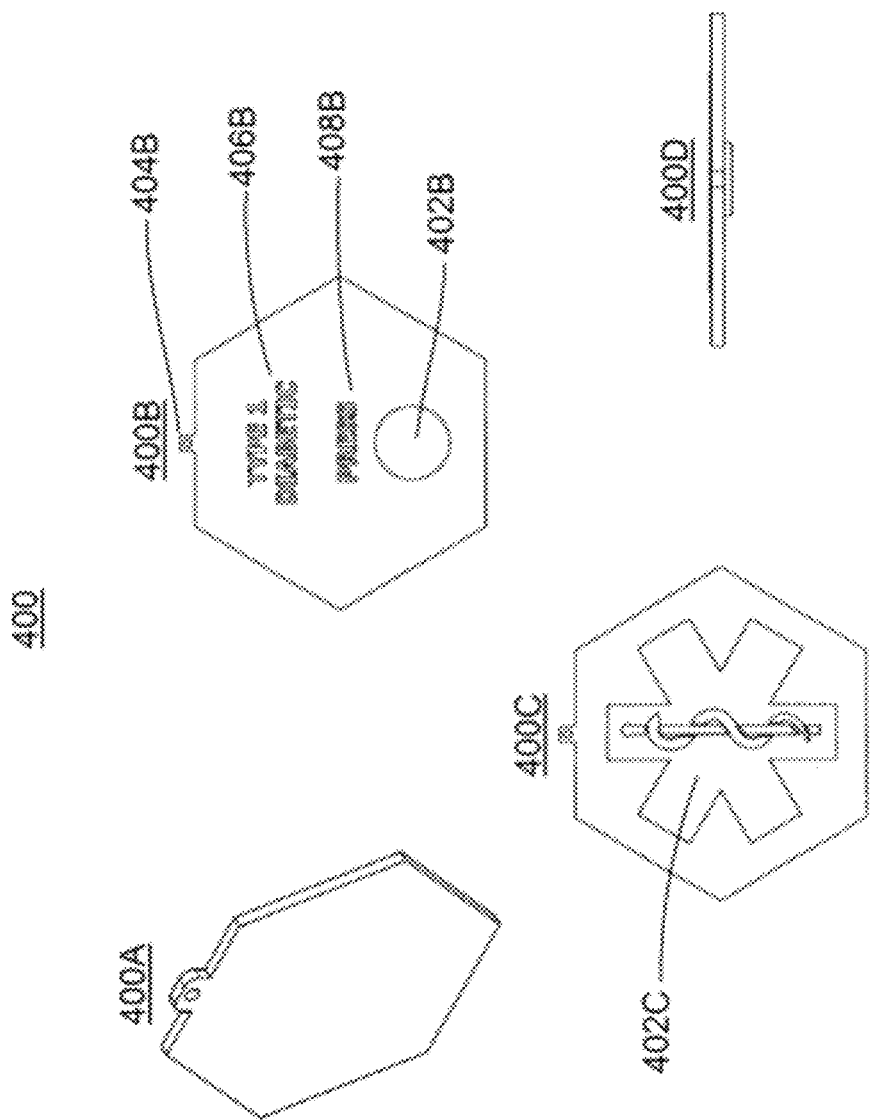

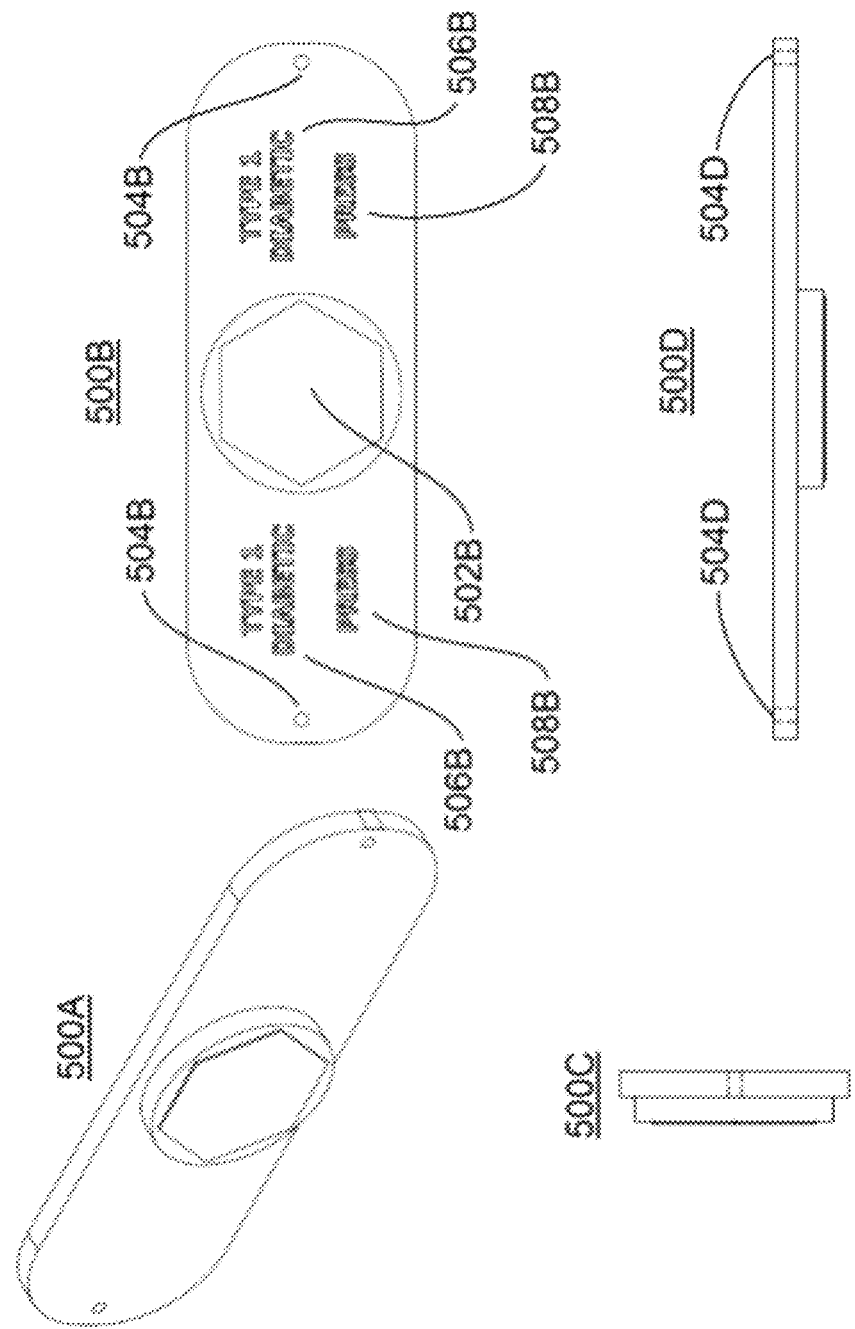

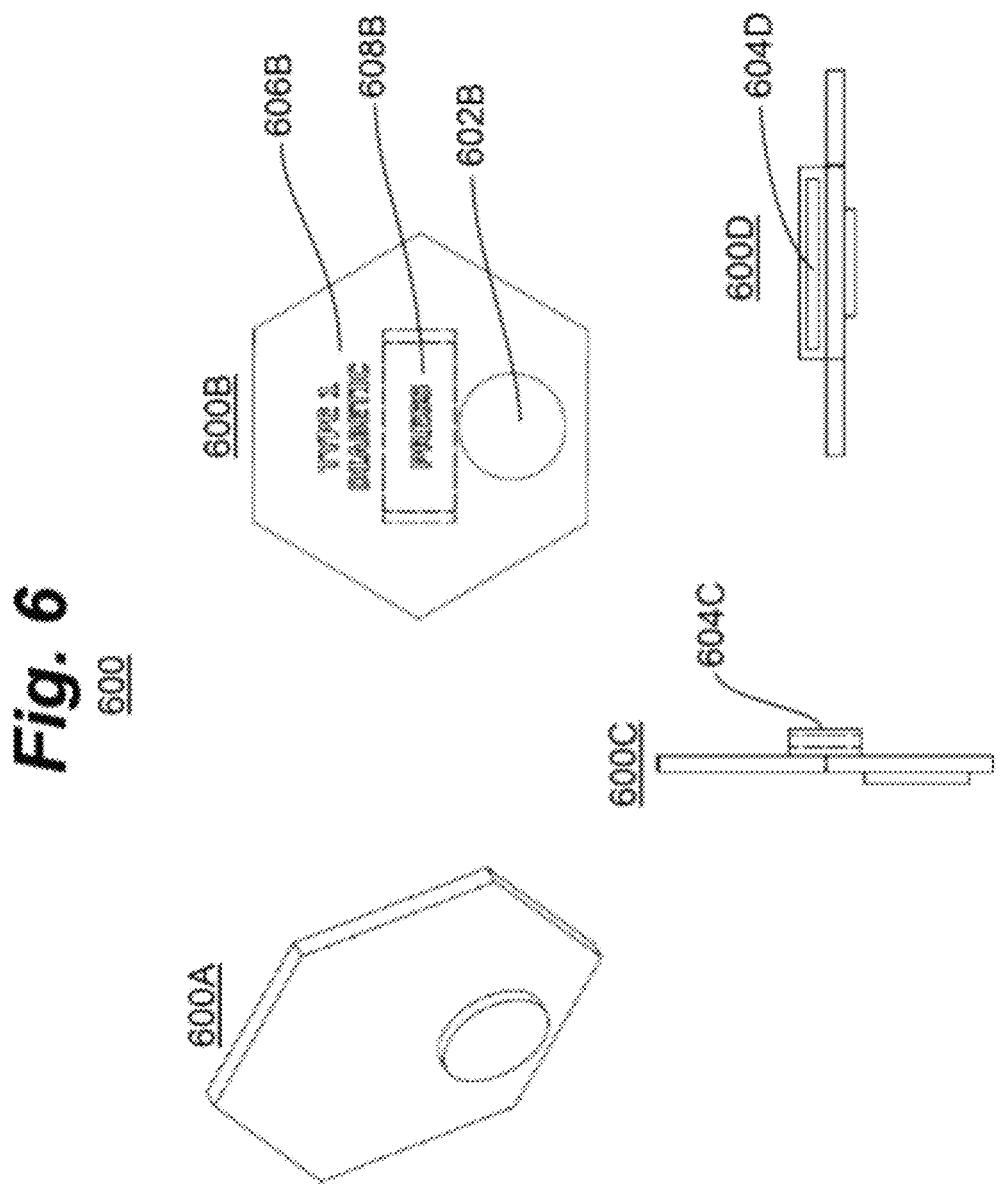

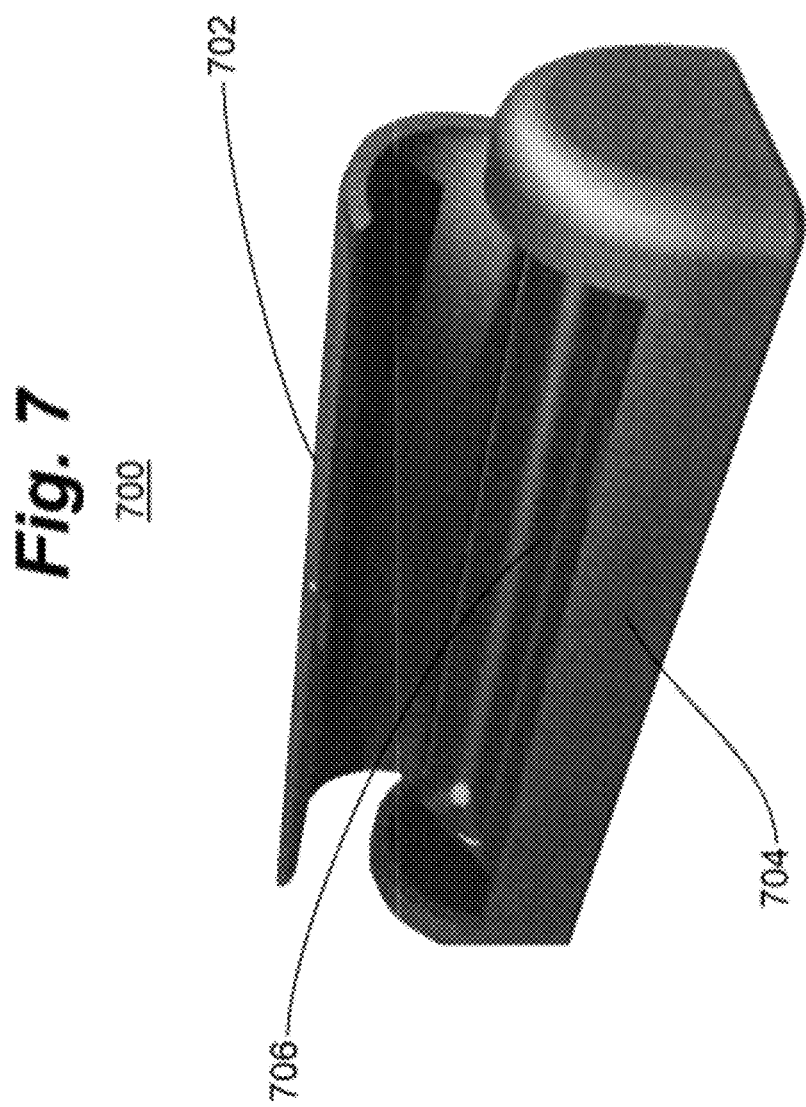

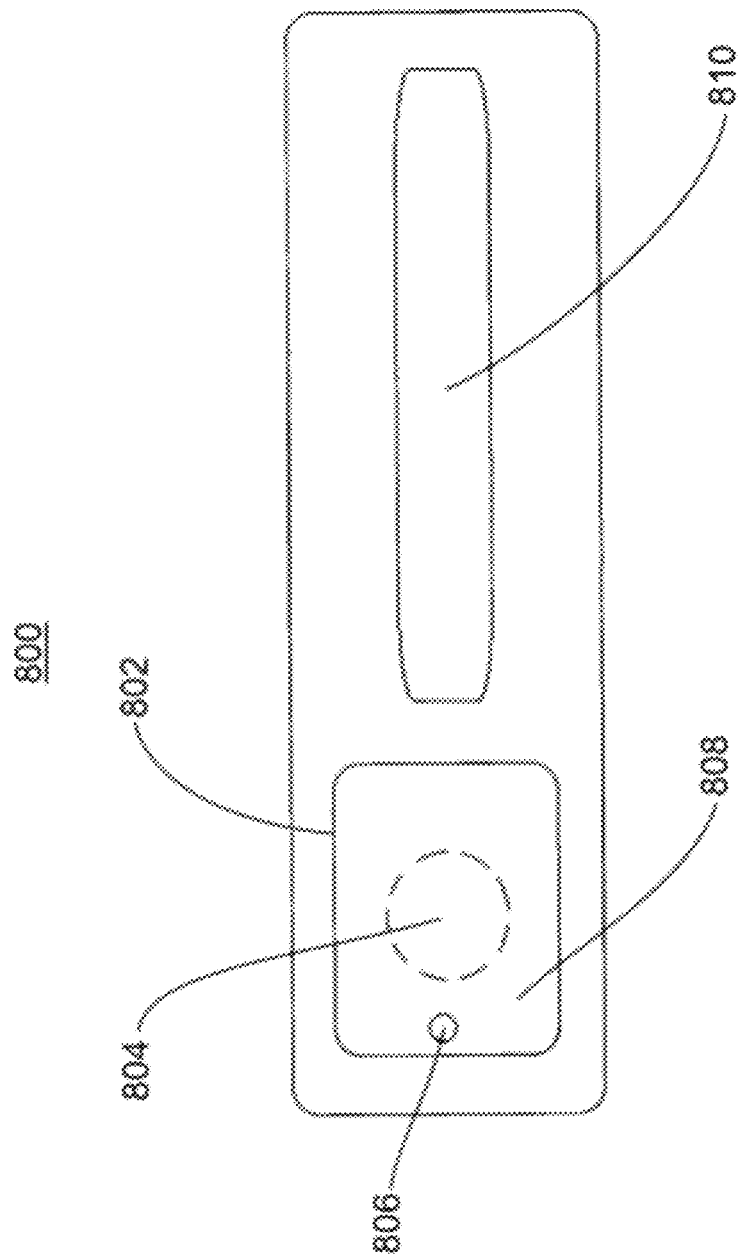

MEDICAMENT KIT AND METHOD OF USE

RELATED APPLICATIONS

This application claims priority to U.S. Provisional Application Ser. No. 61/485,983 filed with the United States Patent and Trademark Office on May 13, 2011 and which is incorporated herein by reference in its entirety.

FIELD OF THE DISCLOSURE

This disclosure relates generally to medical devices and more particularly to kits and methods for providing an injectable medicament.

BACKGROUND

Emergency medicament kits, such as glucagon kits for diabetics or epi-pens for allergies, are life saving devices that contain components necessary to counter the effect of medical problems such as insulin shocks or severe cases of hypoglycemia. These kits usually carry a number of items, such as syringes and various discrete or premixed medications, which need to be administered to the patient. In the case of a patient suffering from an insulin shock, the medication needed is glucagon. However, when a patient is under shock or other distress due to such medical conditions, the patient may not be able to direct a person who is trying to help to the location of the patient's medicament kit. Additionally, the patient may not be able to tell the assisting person how to use the kit. Thus, there is a need for a kit that is easy to locate and a medicament delivery device that is simple to operate. As used throughout this specification, 'patient' or 'person' may be used interchangeably, and should not be construed to limit the invention to use by or for a particular individual.

SUMMARY

In one embodiment of the disclosure, the medicament system comprises a medicament, a medicament delivery device, for example, an injection pen or syringe, an alerting device, operating instructions, and a carrying case. The medicament can be glucagon or some other medicament.

In another embodiment of the disclosure, where a person assisting a patient in medical distress is attempting to locate the patient's medicament delivery device, the assisting person first reads instructions on an alerting device to press an emergency button. The assisting person then presses the emergency button. This in turn sends a signal from the alerting device to an electronic receiver in a carrying case. The electronic receiver then directs circuitry to enable an alarm sounding system to emit an alarm signal in the carrying case. This alarm then attracts the attention of an assisting person to the whereabouts of the carrying case. The assisting person then opens the carrying case and reveals the medicament delivery device. In an example, the medicament delivery device is an injection pen or syringe, though other delivery devices are contemplated.

In another embodiment, where a person assisting a patient in medical distress is attempting to provide a medicament to the patient, the assisting person reads or listens to operating instructions for the medicament system. The assisting person pushes an actuator, for example, an activating button, switch, lever and the like, on a medicament injection pen toward a distal end of the pen. This will cause a plunger to move into a first chamber of the pen where the first chamber is filled with diluting solution. The assisting person continues to press the actuator, which creates pressure in the first chamber. This pressure then breaks a seal, for example, a diaphragm, separating the first chamber from a second chamber in the medicament injection pen. The second chamber is filled with a dry medicament and the diluting solution comes in direct contact with the dry medicament. The assisting person then shakes the medicament injection pen to create a mixture of the diluting solution and medicament. The assisting person thrusts a hypodermic needle that is part of the medicament injection pen, into a soft tissue of the patient and activates the actuator until the mixture is completely injected into the patient.

BRIEF DESCRIPTION OF THE DRAWINGS

These as well as other objects and advantages of this disclosure will be more completely understood and appreciated by referring to the following more detailed description of the exemplary embodiments of the disclosure in conjunction with the accompanying drawings of which:

FIG. 3 shows perspective views of an embodiment of a diaphragm;

FIG. 4 shows perspective views of an embodiment of an alerting device used as a necklace;

FIG. 5 shows perspective views of an embodiment of the alerting device used as a wrist band;

FIG. 6 shows perspective views of an embodiment of the alerting device that can be attached to a person's chattel;

FIG. 7 shows a perspective view of an embodiment of a carrying case; and

FIG. 8 shows a perspective view of an embodiment of a bottom portion of the carrying case.

Figure 1:
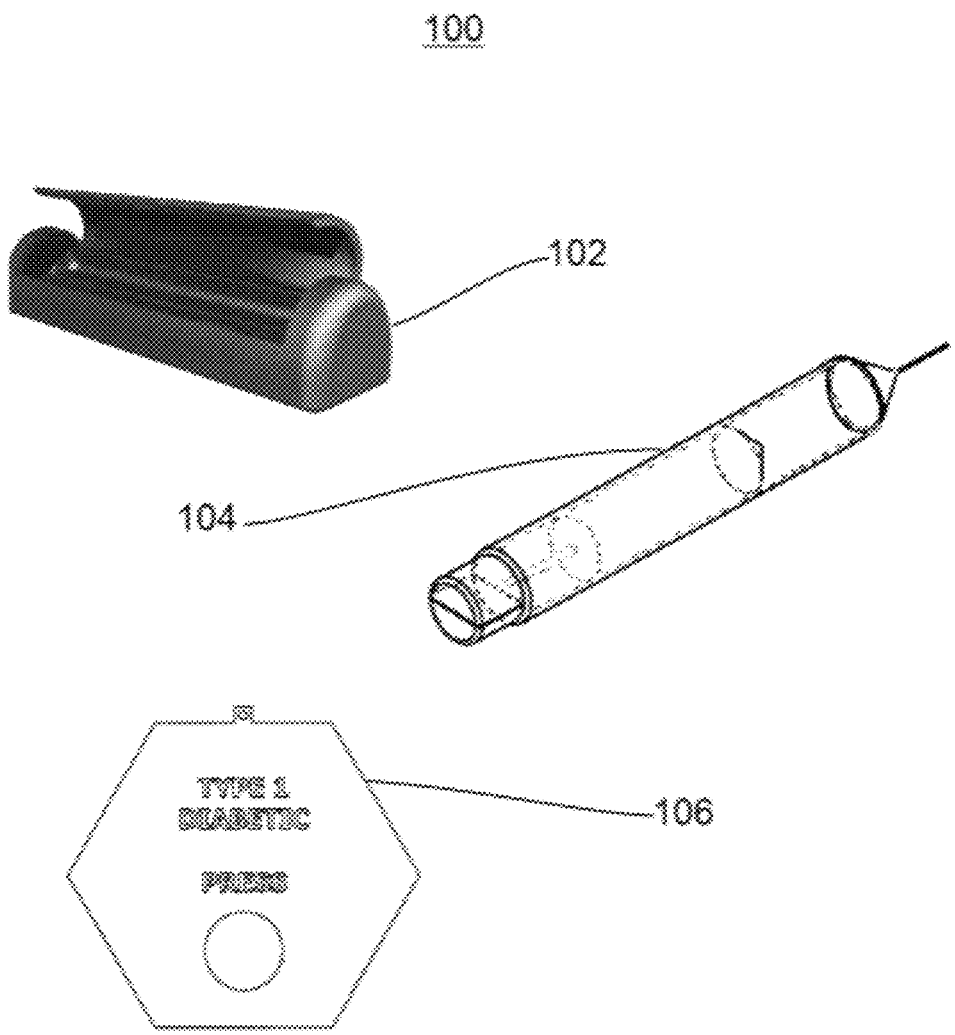
FIG. 1 is a perspective view showing the different components of a medicament kit.

While the disclosure is amenable to various modifications and alternative forms, specifics thereof have been shown by way of example in the drawings and will be described in detail. It should be understood, however, that the disclosure is not to limit the invention to the particular embodiments described. On the contrary, the disclosure is to cover all modifications, equivalents, and alternatives.

DETAILED DESCRIPTION

Advantages and embodiments of this disclosure are illustrated by the following examples, but the particular materials and amounts recited in these examples, as well as other conditions and details, should not be construed to unduly limit this disclosure. The apparatuses and methods disclosed herein may be used to provide a medicament to a person in need of medication. While not meant to be limiting, the systems are illustrated through use of a medicament injection pen. It will be appreciated that the apparatuses and methods are applicable to other medicament delivery devices.

As used in this document, the terms "a" or "an" are used to include one or more than one, independent of any other instances or usages of "at least one" or "one or more." The term "or" is used to refer to a nonexclusive "or", such that "A or B" includes "A but not B," "B but not A," and "A and B," unless otherwise indicated. In addition, the terms "first," "second," "third," etc. are used merely as labels and are not intended to impose any numerical requirement or limitation on their objects. In addition, the terms "including" and "having" and their derivatives, as used in the specification, including the claims, have the same meaning as the word "comprising." The term "in which" is used as the plain-English equivalent of the term "wherein."

FIG. 1 is a perspective view showing the different components of the medicament kit 100. In one embodiment, the kit comprises a carrying case 102, a medicament injection pen 104, and an alerting device 106. In another embodiment, operating instructions for how to use the kit may be printed on the inside of the carrying case 102 or may be included on a tangible medium. Alternatively, operating instructions may be pre-recorded, available to be played by the user. Both the medicament injection pen 104 and any operating instructions are stored in the carrying case 102.

Figure 2:
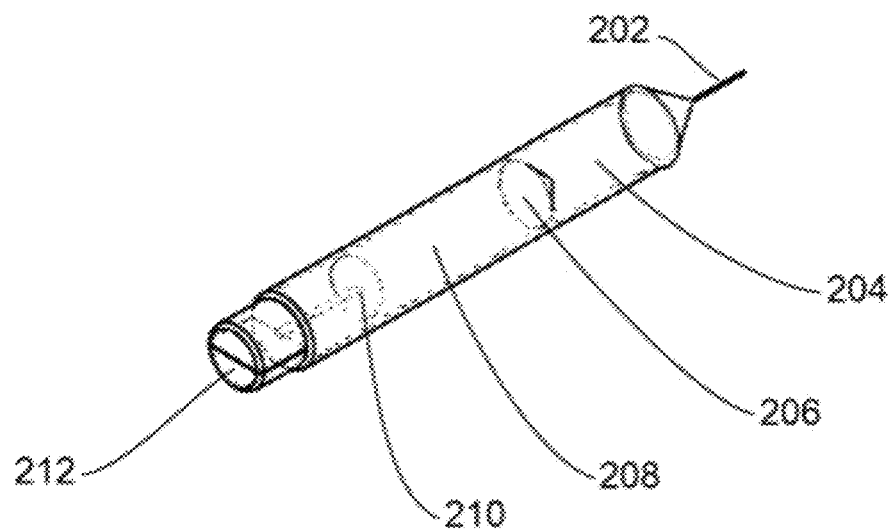
FIG. 2 shows a perspective view of an embodiment of a medicament injection pen.

FIG. 2 shows a perspective view of an embodiment of the medicament injection pen 200. In one embodiment, the medicament injection pen 200 comprises an actuator 212 attached to a plunger 210. The plunger 210 is located in a first chamber 208 that is separated from a second chamber 204 by a diaphragm 206. A hypodermic needle 202 is coupled to the distal end of chamber 204. In one embodiment, chamber 204 contains a medicament and chamber 208 contains a diluting solution liquid. In another embodiment, the medicament can be contained in chamber 208 and the diluting solution can be contained in chamber 204. In another embodiment, a single chamber medicament injection pen can be used for some injection-ready medicaments.

The medicament can be an injectable medicament that may be carried by the patient, or alternatively, can be provided by a medical practitioner. In some instances, the patient can carry the medicament when the medicament may be needed immediately, for example, when the patient is suffering from insulin shock, a severe case of hypoglycemia, or from a severe allergic reaction. In such cases, the medicament can be, for example, dry glucagon, epinephrine, and the like. The example of glucagon as the medicament is provided as an illustrative example; other medicaments are contemplated.

In one embodiment, a method for providing a medicament to a person suffering medical distress may include, an assisting person being directed by the operating instructions printed on the inside of the carrying case 102 or included on a tangible medium. Alternatively, an assisting person may be instructed by pre-recorded instructions emanating from the carrying case 102. The assisting person may be instructed to push the actuator 212 toward the distal end of the syringe (the distal end being at the location of the hypodermic needle 202) and into a first chamber 208. The actuator may be mechanically coupled to a plunger, or the actuator may be coupled to a cylindrical member in turn coupled to a plunger. The plunger can exert pressure on a fluid in the first chamber, and includes a seal to prevent fluid from leaking out of the first chamber. Pushing the actuator has the effect of pushing the plunger 210 into a first chamber 208 and creating pressure on diaphragm 206. The pressure can break diaphragm 206 and allow the first chamber 208 and second chamber 204 to become in fluid communication with each other. Accordingly, the diluting solution in a first chamber and medicament in a second chamber can mix. The actuator and plunger can indicate when they have traveled a distance sufficient to break the diaphragm, for example, by mechanical interference, by markings on the injector pen 200, or by a tactile or audible indication. The assisting person may then be instructed to gently shake the medicament injection pen 200 and then thrust the hypodermic needle 202 into a soft tissue of the person suffering medical distress. The assisting person may then be instructed to further push the actuator 212 so that the mixture is injected completely into the person. In another embodiment, the syringe may have only one chamber, the chamber containing injection-ready medicament. In this case, the medicament is injected into the person suffering medical distress in a similar way, but without the need for mixing the medicament before injection.

FIG. 3 shows perspective views of an embodiment of the diaphragm 206. The diaphragm 206 is shown in a closed front view 300A from distal needle end, closed side view 300B, open front view 300C from distal needle end, and open side view 300D. In one embodiment, the diaphragm 206 can be made of plastic such as polystyrene, polypropylene, high-density polyethylene, or any other suitable material susceptible to fracture, breaking or puncture under pressure. In one embodiment, the design of the diaphragm 206 is cone shaped and is scored 302A/302B into fourths that serve as stress points. When pressure is increased on the closed diaphragm 300A/300B, the scored lines 302A/302B will eventually break and become broken slits 302D. The diaphragm 206 will then become an open diaphragm 300C/300D and allow the diluting solution and medicament to mix.

FIG. 4 shows perspective views of an embodiment of the alerting device 106 used as a necklace. The alerting device 106 is shown in a 3-dimensional view 400A, front view 400B, back view 400C, and side view 400D. In one embodiment, the alerting device 400 is hexagonal shaped, but other shapes, for example, round, rectangular, and the like are contemplated. In one embodiment, the alerting device 400 indicates that the patient is a Type 1 diabetic 406B and provides instructions to press 408B an emergency button 402B. In another embodiment, other types of medical conditions can be listed on the alerting device 400, for example, "Peanut allergy." In another embodiment, the back view 400C of the alerting device 400 may display the universal medical sign 402C.

In one embodiment, the alerting device 400 has a front and back side, wherein both sides can be snapped into or coupled to each other by frictional means or mechanical means. In another embodiment, the alerting device 400 has an aperture 404B which passes through the front and back sides, wherein the aperture 404B is adapted to accept a length of material, for example, a chain, string, leather strip, and the like, to form a necklace that can suspend the alerting device 400 around the neck of the patient. The front and back sides may enclose a battery compartment, battery, part of the emergency button 402B and electronic circuitry. In one embodiment, the battery is a standard circular 3 volt battery.

In one embodiment, a method for locating a medicament delivery device 104 is described, wherein the assisting person first reads the instructions on an alerting device 400 to press 408B the emergency button 402B. The assisting person presses the emergency button 402B and the alerting device 400 produces an electromagnetic wave through the air. The frequency of this electromagnetic wave is picked up by an electronic receiver located in the carrying case 102. The electronic receiver triggers an alarm sounding system or flashing light, for example a flashing light emitting diode (LED) in the carrying case 102 (to be discussed in more depth with respect to FIG. 8). The assisting person's attention is attracted to the beeping alarm and/or flashing LED. Thus, the assisting person becomes aware of the location of the carrying case 102 amongst the patient's belongings. For example, the carrying case 102 may be in a purse or briefcase. The assisting person opens the carrying case 102, and the medicament injection pen 200 and operating instructions are revealed.

FIG. 5 shows perspective views of an embodiment of an alerting device 500 used as a wrist band. The alerting device 500 is shown in a 3-dimensional view 500A, front view 500B, first side view 500C, and second side view 500D. In one embodiment, the alerting device 500 is rectangular shaped with rounded edges. In one embodiment, the alerting device 500 indicates that the patient is a Type 1 diabetic 506B and provides instructions to press 508B an emergency button 502B. In another embodiment, other types of medical conditions can be listed on the alerting device, for example, "Peanut allergy." In another embodiment, the back view of the alerting device may display the universal medical sign (see 402C in FIG. 4).

In one embodiment, the alerting device 500 has a front and back side, wherein both sides can be snapped into each other by frictional means. In another embodiment, the alerting device 500 has two apertures 504B/504D which pass through the front and back sides, wherein each aperture 504B/504D is adapted to accept a length of material, for example, a chain, string, leather strip, and the like, to form a wrist band that can suspend the alerting device 500 around the wrist of the patient. The front and back sides may enclose a battery compartment, battery, part of the emergency button 502B and electronic circuitry. In one embodiment, the battery is a standard circular 3 volt battery. The method for locating a medicament injection pen 200 using the wrist band alerting device 500 is analogous to that described for a necklace.

FIG. 6 shows perspective views of an embodiment of the alerting device 600 that can be attached to a person's chattel. The alerting device 600 is shown in a 3-dimensional view 600A, front view 600B, first side view 600C, and second side view 600D. In one embodiment, the alerting device 600 is hexagonal shaped, however other shapes are possible and contemplated. In one embodiment, the alerting device 600 indicates that the patient is a Type 1 diabetic 606B and provides instructions to press 608B an emergency button 602B. In another embodiment, other types of medical conditions can be listed on the alerting device, for example, "Peanut allergy." In another embodiment, the back view of the alerting device 600 may display the universal medical sign (see 402C in FIG. 4).

In one embodiment, the alerting device 600 has a front and back side, wherein both sides can be snapped into each other by frictional means or otherwise coupled to each other by mechanical means. In another embodiment, the alerting device 600 has a slot 604C-604D attached to the back side, wherein the slot 604C-604D provides a means to attach the alerting device to the patient's belt loop, clothing, purse, bag, briefcase, keychain or other chattel. The front and back sides may enclose a battery compartment, battery, part of the emergency button 602B and electronic circuitry. In one embodiment, the battery is a standard circular 3 volt battery. The method for locating a medicament injection pen using the chattel-attaching alerting device is analogous to that described in association with FIG. 4.

FIG. 7 shows a perspective view of an embodiment of the carrying case 700. The carrying case 700 comprises a cover 702 attached to a main case body 704. A portion of the main case body 704 comprises the bottom portion of the carrying case 706. In one embodiment, the cover 702 is dome shaped. In one embodiment, the cover 702 is attached to the main case body 704 via a hinge. There may be one hinge attached to each lateral end of the cover 702. Both hinges can attach to the main case body 704 and the cover 702 is held in place. The hinge attachment allows the cover to rotate into open and closed positions. In another embodiment, the cover 702 is attached to the main case body 704 via a peg. On each inner end of the main case body 704, a peg extends laterally toward the center of the case. On each outer end of the cover 702, a corresponding hole is present which runs laterally toward each outer end. Each hole has a slightly larger diameter than each corresponding peg. Each peg on the main case body 704 fits into its corresponding hole on the cover 702 and the cover 702 is held in place. The peg attachment allows the cover 702 to rotate into open and closed positions. In one embodiment, when the cover 702 moves into the closed position using either the hinge or peg attachment mechanism, the cover 702 fastens with the main case body 704 in a snapping fashion. Other case closure methods are known in the art and are included in this disclosure.

FIG. 8 shows a perspective view of an embodiment of the bottom portion of the carrying case 800. The bottom portion of the carrying case 800 can comprise two compartments. One compartment is an elongated compartment 810 that is designed to house the medicament injection pen 200 (see FIG. 2) and operating instructions. The second compartment is an electronics compartment 802 that houses at least one battery, an electronic receiver, an alarm sounding system, an LED, and all required circuitry. In one embodiment, the alarm sounding system rests over a circular hole 804 formed in the bottom portion of the carrying case 800. The hole can have a constant or varying diameter as depth increases. The circular hole 804 can increase the perceived volume of the alarm sounding system and may make the alarm more audible. In one embodiment, the battery is a standard circular 3 volt battery. On top of the electronics compartment 802 is a cover 808 locked by a fastener 806.

In one embodiment, a method for locating a medicament injection pen 200 can include an actuator being activated, for example, an emergency button being pressed, sending a signal. The frequency of the produced electromagnetic wave is picked up by the electronic receiver. The receiving antenna on the electronic receiver picks up radiation from the electromagnetic waves. One skilled in the art should recognize that the signal from the alerting device 400A-400D (see FIG. 4) is synchronized with the electronic receiver. A radio receiver on the electronic receiver converts the radiation into usable form. This information is then decoded and used by the electronic receiver to turn on the circuit. The circuit activates the alarm sounding system or flashing light (e.g. LED) which attracts the attention of the assisting person to the whereabouts of the carrying case 700 (see FIG. 7).

In one embodiment, the circuit runs on direct current voltage and comprises resistors, timers, capacitors, grounding, and a speaker. In another embodiment, the circuit runs on direct current voltage and comprises a capacitor, a diode, grounding, a speaker, a resistor, and a switch.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, feature locations, etc. have been described for use with disclosed embodiments, others besides those disclosed may be utilized without exceeding the scope of the invention.

Persons of ordinary skill in the relevant arts will recognize that the invention may comprise fewer or combinations of features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

What is claimed is:

1. A medicament delivery system comprising:
    a medicament;
    a medicament delivery device comprising an injection pen comprising an actuator attached to a plunger and a diaphragm, where at least one of the actuator and the plunger indicate a distance sufficient to break the diaphragm, wherein the diaphragm is cone-shaped and scored;
    a carrying case, wherein a location alarm system is housed in the carrying case; and
    a personal wearable alerting device;
    wherein the personal wearable alerting device further comprises;
        a front side, wherein an emergency button configured to send an alert signal from the personal wearable alerting device to the location alarm system, instructions to press the emergency button, and text indicating the patient's medical condition are disposed on the front side;
        a back side opposite the front side, wherein medical identification symbol is disposed on the back side;
        a first battery disposed between the front side and the back side; and
        a first electronic circuitry disposed between the front side and the back side, wherein the first electronic circuitry is capable of emitting electromagnetic radiation;
    wherein the carrying case further comprises:
        a main case body wherein the main case body comprises an elongated compartment, wherein the elongated compartment is adapted to house the medicament delivery device and operating instructions;
        an electronics compartment;
        an electronic receiver, wherein the electronic receiver is housed in the electronics compartment, is adapted to receive and decode electromagnetic radiation, and is electronically connected to the location alarm system;
        a second battery coupled to a second circuitry;
        a first cover coupled to the electronics compartment; and
        a second cover coupled to the main case body.

2. The medicament delivery system of claim 1, wherein the medicament is glucagon.

3. The medicament delivery system of claim 1, wherein the medicament delivery device comprises:
    a single chamber containing the medicament, wherein the medicament is an injection-ready medicament;
    a hypodermic needle coupled to a distal end of the chamber;
    the actuator coupled to a proximal end of the chamber; and
    the plunger coupled to the actuator, wherein the plunger is disposed in the chamber.

4. The medicament delivery system of claim 1, wherein the personal wearable alerting device further comprises at least one aperture passing through the front side and the back side of the alerting device.

5. The medicament delivery system of claim 1, wherein the text indicating the patient's medical condition indicates the patient's medical condition is Type 1 diabetes.

6. The medicament delivery system of claim 1, wherein the electromagnetic radiation emitted by the personal wearable alerting device is received by the electronic receiver of the carrying case, thus activating the location alarm system.

7. The medicament delivery system of claim 1, wherein the location alarm system emits an aural alarm or a visual alarm.

8. The medicament delivery system of claim 1, wherein the second cover is attached to the main case body with a peg.

9. The medicament delivery system of claim 1, wherein the personal wearable alert device is configured as a necklace.

10. The medicament delivery system of claim 1, wherein the operating instructions are pre-recorded so that the operating instructions are playable by a user.

11. The medicament delivery system of claim 1, wherein the medicament is epinephrine.

12. The medicament delivery system of claim 1, wherein the personal wearable alert device is configured as a bracelet.

13. The medicament delivery system of claim 1, wherein the personal wearable alert device is configured so that it is attachable to a person's chattel.

14. The medicament delivery system of claim 1, wherein the first electronic circuitry runs on direct current voltage and comprises resistors, timers, capacitors, grounding, and a speaker.

15. The medicament delivery system of claim 1, wherein the first electronic circuitry runs on direct current voltage and comprises a capacitor, a diode, grounding, a speaker, a resistor, and a switch.

16. The medicament delivery system of claim 1, wherein the medicament delivery device comprises:
    a chamber;
    the diaphragm susceptible to breaking under pressure disposed between the distal end of the chamber and the proximal end of the chamber, wherein the diaphragm divides the chamber into a first chamber and a second chamber;
    a hypodermic needle in fluid communication with the distal end of the chamber;
    the actuator in communication with a proximal end of the chamber; and
    the plunger coupled to the actuator wherein the plunger is disposed in the first chamber.

17. The medicament delivery system of claim 16, wherein the first chamber contains a diluting solution and the second chamber contains the medicament in dry form.

18. The medicament delivery system of claim 16, wherein the diaphragm is made of plastic.

19. A method for using a medicament delivery system, comprising:
    pressing an emergency button on a personal wearable alerting device;
    sending a signal from the personal wearable alerting device to an electronic receiver in a carrying case;
    directing circuitry within the carrying case to allow an alarm system within the carrying case to emit an alarm signal;

attracting the attention of an assisting person to the whereabouts of the carrying case;
opening the carrying case; and
revealing a medicament injection pen comprising an actuator attached to a plunger and a diaphragm, where at least one of the actuator and the plunger indicate a distance sufficient to break the diaphragm, wherein the diaphragm is cone-shaped and scored.

20. The method of claim 19, further comprising:
pushing the actuator toward a distal end of the medicament injection pen;
causing the plunger to travel in the medicament injection pen into a first chamber filled with a diluting solution;
creating pressure in the first chamber to break the diaphragm, wherein the diagram divides a chamber in the medicament injection pen into the first chamber and a second chamber, wherein the second chamber is filled with a dry medicament;
breaking the diaphragm wherein the diluting solution comes in direct contact with the dry medicament;
shaking the medicament injection pen to create a mixture of the diluting solution and the dry medicament;
thrusting a hypodermic needle at the distal end of the medicament injection pen into a muscle of a patient; and
pushing the actuator until the mixture is completely injected into the muscle of the patient.

* * * * *